US00PP36238P2

(12) United States Plant Patent
Yencho et al.

(10) Patent No.: US PP36,238 P2
(45) Date of Patent: Nov. 5, 2024

(54) SWEETPOTATO PLANT NAMED 'NCORNSP-032SCRHI'

(50) Latin Name: ***Ipomoea batatas* (L.) Lam**
Varietal Denomination: NCORNSP-032SCRHI

(71) Applicant: North Carolina State University, Raleigh, NC (US)

(72) Inventors: George Craig Yencho, Raleigh, NC (US); Kenneth Vincent Pecota, Raleigh, NC (US); Christopher Heim, Morrisville, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 18/420,834

(22) Filed: Jan. 24, 2024

(51) Int. Cl.
*A01H 5/12* (2018.01)
*A01H 6/00* (2018.01)

(52) U.S. Cl.
USPC ..... Plt./258

(58) Field of Classification Search
USPC ..... Plt./226, 258
See application file for complete search history.

*Primary Examiner* — Susan McCormick Ewoldt
(74) *Attorney, Agent, or Firm* — Myers Bigel, P.A.

(57) ABSTRACT

'NCORNSP-032SCRHI' is a moderately compact and loosely upright variety with a moderate growth rate and is well branched. It is distinguishable from other ornamental sweetpotato cultivars by its red to burgundy five lobed leaves, a moderately-compact habit and semi-erect mounding plant architecture. The burgundy leaves, uniform color, short internodes, and the plant architecture, which promotes good plant production in the greenhouse for wholesale distributors, distinguishes 'NCORNSP-032SCRHI' amongst the current ornamental sweetpotatoes in the marketplace. In greenhouse and field trials, 'NCORNSP-032SCRHI' is shown to be suitable for use as a landscape or containerized plant. The production of flowers by 'NCORNSP-032SCRHI' is not observed under short-day conditions.

6 Drawing Sheets

Name of the genus and species: The Latin name of the novel, ornamental plant variety disclosed herein is *Ipomoea batatas* (L.) Lam.

Variety denomination: The inventive cultivar of *Ipomoea batatas* disclosed herein has been given the varietal denomination 'NCORNSP-032SCRHI'.

BACKGROUND OF THE INVENTION

*Ipomoea batatas* is a member of the morning glory family Convolvulaceae. This species is grown worldwide, and it exhibits a wide range of plant forms and colors. The cultivated members of *Ipomoea batatas* grown by farmers worldwide are commonly produced for consumption of their nutritious, enlarged storage roots. These types typically produce a fast-growing green vine that has a wide variety of leaf shapes ranging from palmate and deeply lobed, to cordate or triangular shaped leaves with no lobes.

Like their edible forms, *Ipomoea batatas* ornamental sweetpotato plants are a heat-loving, drought-tolerant, perennial vine typically grown as an annual. However, ornamental sweetpotato plants are distinguished from the edible cultivated forms in that they often do not produce attractive, enlarged storage roots suitable for human consumption. Instead, they possess unique foliage colors, leaf shapes, and growth habits, which have significant value in the ornamental marketplace.

Ornamental sweetpotatoes are desirable in the landscape and ornamental industries because their foliage comes in a wide variety of colors (e.g., pale yellow to dark purple with some exhibiting temporal and individual leaf color variegation patterns) and plant shapes (e.g., mounded and very compact to prostrate and highly spreading). They can be grown in a potted plant and/or mixed planting format, and they can cover a large space or hang over walls and decorative pots creating brightly colored and textured backdrops in gardens and patios. Most ornamental sweetpotatoes grow and last the entire growing season and they require little maintenance. Moreover, these plants have few insect or disease problems.

To meet the growing horticultural demand for ornamental sweetpotatoes, it is desirable to produce new cultivars of ornamental sweetpotato with new or improved foliage colors, variegation patterns, leaf shapes, and plant architectures. In addition, it would be advantageous to develop cultivars of ornamental sweetpotato exhibiting a more compact growth that do not out-compete other species in mixed containers.

'NCORNSP-032SCRHI' was bred to meet the demand for new ornamental sweetpotatoes. 'NCORNSP-032SCRHI' is a moderately compact and loosely upright variety with a moderate growth rate and is well branched. It is distinguishable from other ornamental sweetpotato cultivars by its red to burgundy five-lobed leaves, a moderately-compact habit and semi-erect mounding plant architecture. The burgundy leaves, uniform color, short internodes, and the plant architecture, which promotes good plant production in the greenhouse for wholesale distributors, distinguishes 'NCORNSP-032SCRHI' amongst the current ornamental sweetpotatoes in the marketplace. In greenhouse and field trials conducted since 2020 by the breeding program and industry collaborators 'NCORNSP-032SCRHI' has been shown to be less vigorous than *Ipomoea batatas* 'Marchgarita' (unpatented) and 'Blackie' (unpatented) and is suitable for use as a landscape or containerized plant. The production of flowers by 'NCORNSP-032SCRHI' is not observed under short day conditions.

Lineage. 'NCORNSP-032SCRHI' (breeding designation 'NC10438-001ORN') originated from open-pollinated seed from the proprietary *Ipomoea batatas* breeding line 'NC9729-169ORN' (the female parent; not patented). Botanical seed was harvested from a open-pollinated breeding nursery of ornamental lines grafted onto a flower-inducing *I. setosa* Brazilian morning glory line that were maintained in the field between May 2019 and November 2019 in Clinton, North Carolina. 'NC9729-169ORN' resulted from open-pollinated seed harvested from the proprietary *Ipomoea batatas* breeding line 'NC8967-011ORN' (the female parent; not patented). Botanical seed from this family were planted in the greenhouse in February 2020. The first cycle of selection on the population was exercised at the seedling tray stage and each survivor was transferred to a single 6-inch pot, which was then maintained in the greenhouse. Cuttings (2 each) were taken from the plants in April and planted in the field as unreplicated 2-plant plots, during mid-June 2020. The single, individual plant now known as 'NCORNSP-032SCRHI' was selected Sep. 25, 2020, because of its combination of exceptional features, and it has been propagated asexually since that time.

Asexual Reproduction. Since its selection, *Ipomoea batatas* 'NCORNSP-032SCRHI' has been asexually reproduced in Raleigh, North Carolina predominantly by vegetative propagation of vine cuttings. Successively, there have been six cycles of vegetative propagation, one cycle of tissue culture micropropagation, and multiple vegetative propagation cycles to increase plant numbers. Asexual reproduction of 'NCORNSP-032SCRHI' by cuttings has shown that the unique features of the new cultivar are stable, and the plant reproduces true to type in successive generations.

SUMMARY OF THE INVENTION

'NCORNSP-032SCRHI' was bred to meet the demand for new ornamental sweetpotatoes. 'NCORNSP-032SCRHI' is a moderately compact and loosely upright variety with a moderate growth rate and is well branched. It is distinguishable from other ornamental sweetpotato cultivars by its red to burgundy five-lobed leaves, a moderately-compact habit and semi-erect mounding plant architecture. The burgundy leaves, uniform color, short internodes, and the plant architecture, which promotes good plant production in the greenhouse for wholesale distributors, distinguishes 'NCORNSP-032SCRHI' amongst the current ornamental sweetpotatoes in the marketplace. In greenhouse and field trials conducted since 2020 by the breeding program and industry collaborators 'NCORNSP-032SCRHI' has been shown to be less vigorous than *Ipomoea batatas* 'Marchgarita' and 'Blackie' and is suitable for use as a landscape or containerized plant. The production of flowers by 'NCORNSP-032SCRHI' is not observed under short-day conditions.

BRIEF DESCRIPTION OF THE DRAWINGS

The photographs in the drawings were made using conventional techniques and show the colors as true as reasonably possible by conventional photography. Colors in the photographs may differ slightly from the color values cited in the detailed botanical description, which more accurately describe the colors of the new *Ipomoea batatas*.

DETAILED BOTANICAL DESCRIPTION OF THE NEW VARIETY

Figure 1:
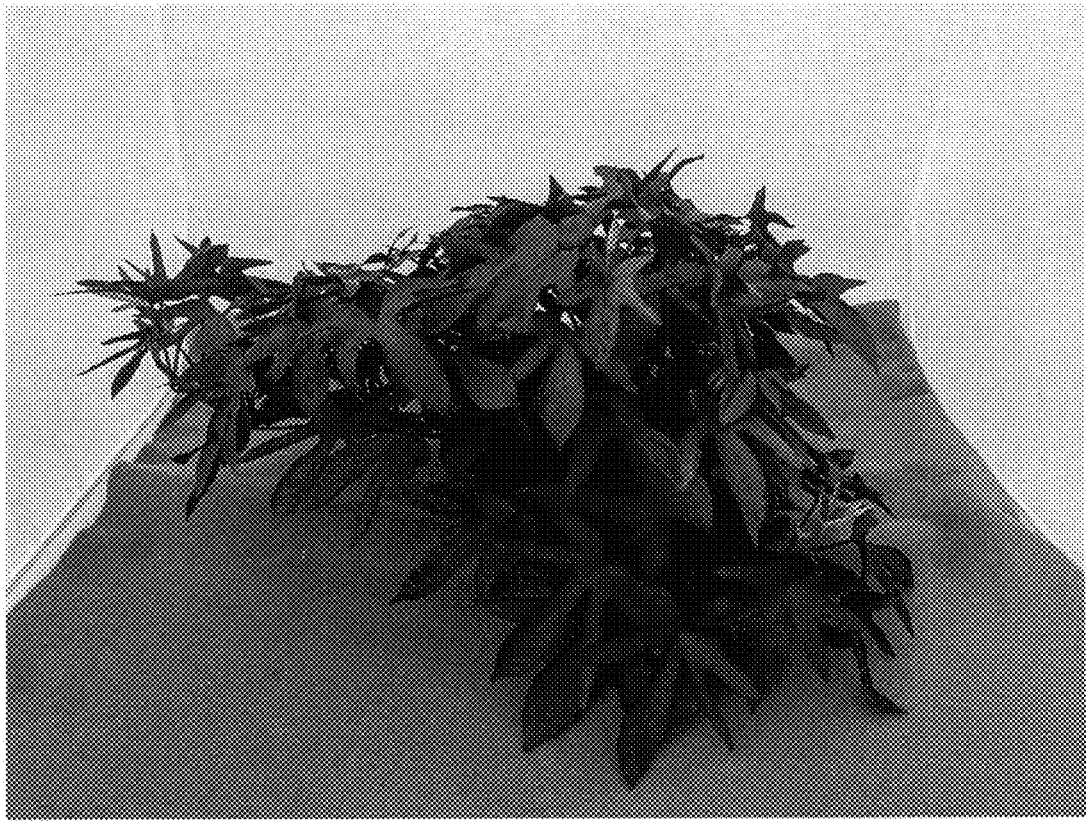
FIG. 1 is a color photograph of a typical specimen of greenhouse grown *Ipomoea batatas* 'NCORNSP-032SCRHI' in a 6-inch pot from the side, 58 days after planting.
Figure 2:
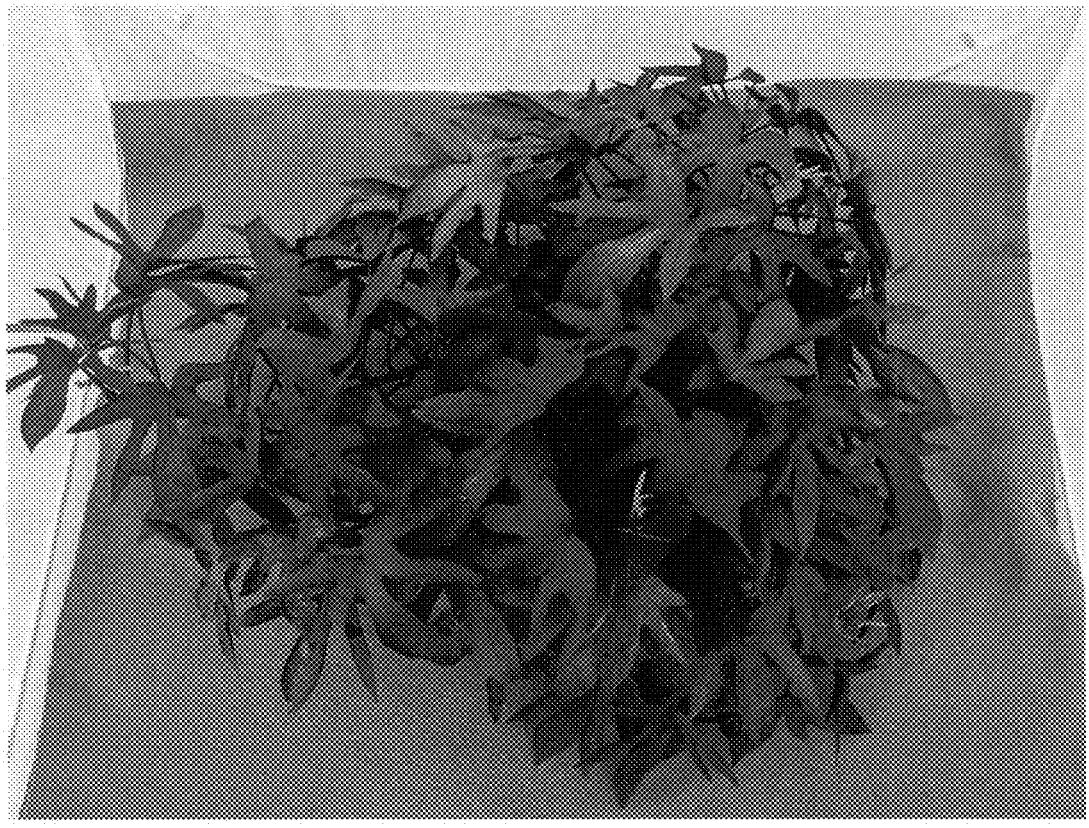
FIG. 2 is a color photograph of a typical specimen of greenhouse grown *Ipomoea batatas* 'NCORNSP-032SCRHI' in a 6-inch pot from the top, 58 days after planting.
Figure 3:
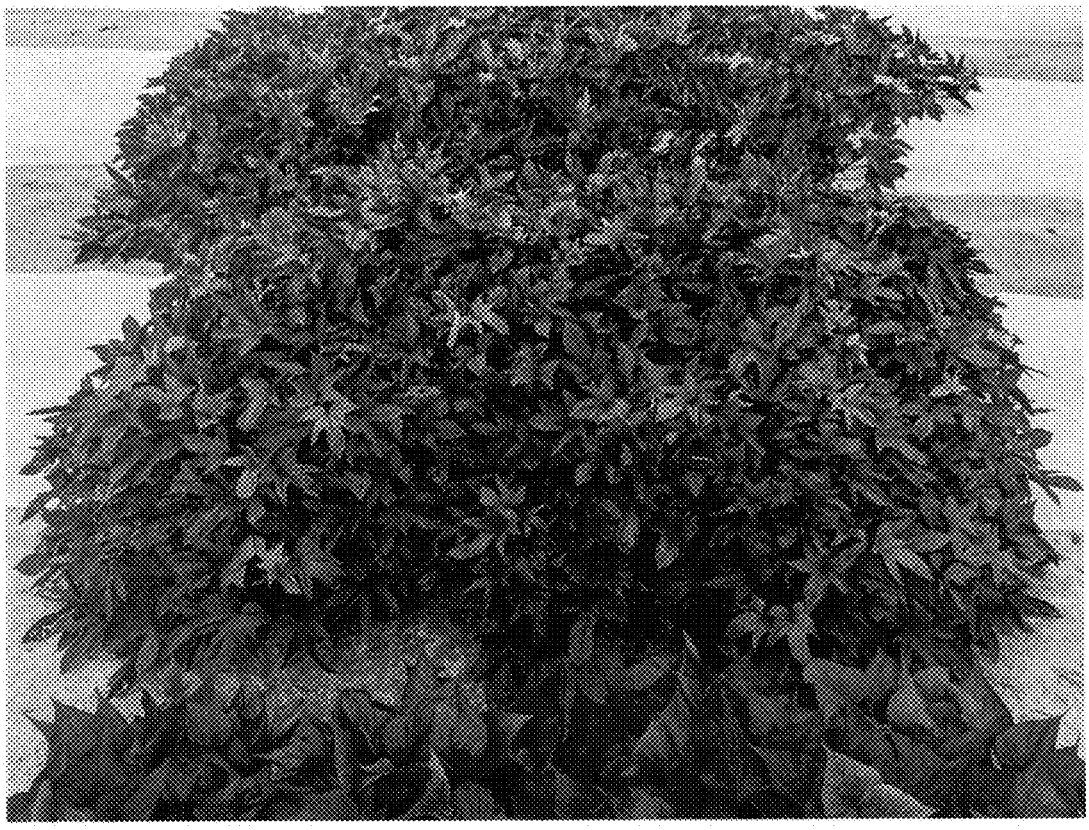
FIG. 3 is a color photograph of a typical specimen of *Ipomoea batatas* 'NCORNSP-032SCRHI' from the side in the field, 63 days after planting.
Figure 4:
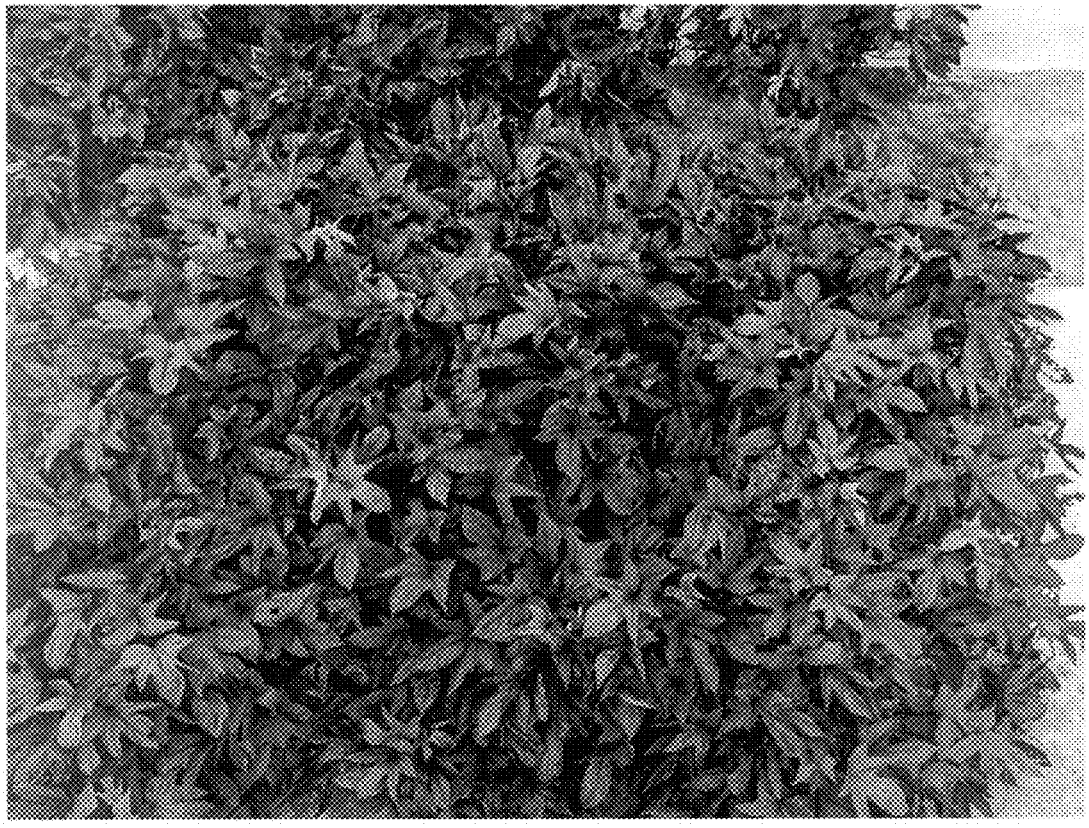
FIG. 4 is a color photograph of a typical specimen of *Ipomoea batatas* 'NCORNSP-032SCRHI' from the top in the field, 63 days after planting.
Figure 5:
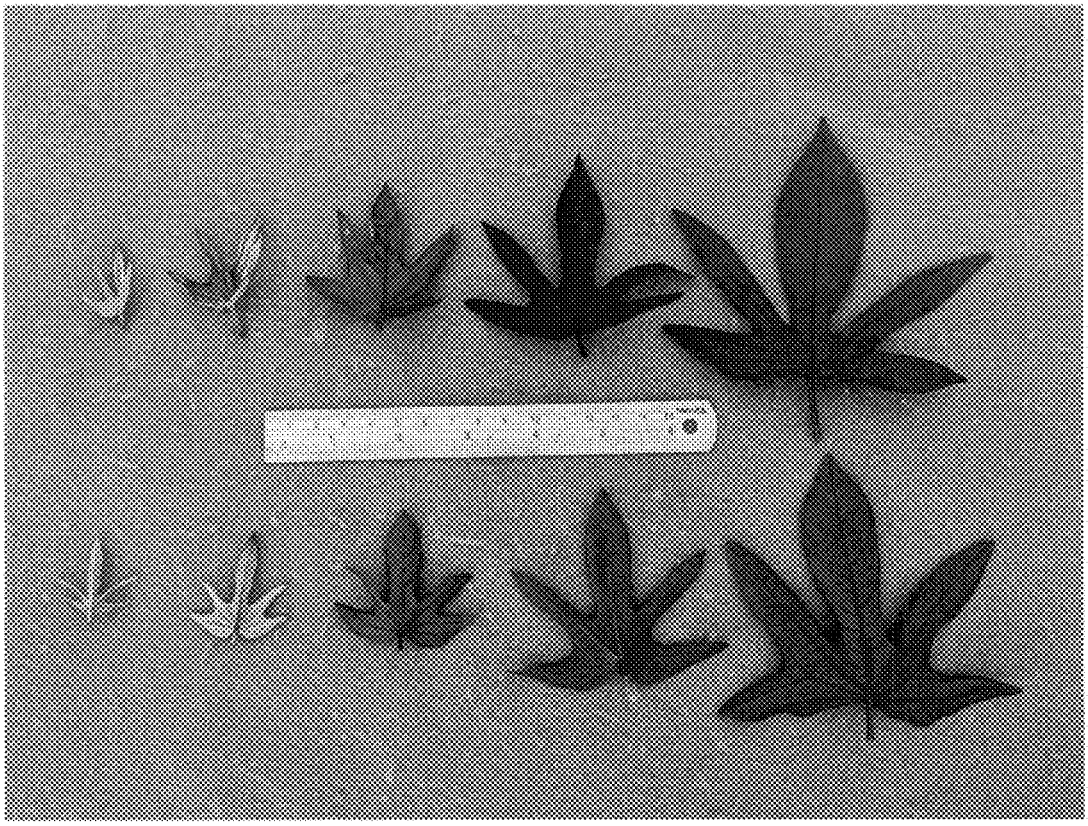
FIG. 5 is a color photograph showing the upper (top) and lower (bottom) surfaces of mature leaves produced by greenhouse grown *Ipomoea batatas* 'NCORNSP-032SCRHI', 58 days after planting.

The following is a detailed description of the botanical characteristics of a new and distinct cultivar of *Ipomoea batatas* plant known by the cultivar name 'NCORNSP-032SCRHI'. All colors cited herein refer to The Royal Horticulture Society Colour Chart designations (The Royal Horticultural Society, London, 1995, $4^{th}$ ed.) except where general terms of ordinary dictionary significance are used. Plant descriptions are based on the standardized international sweetpotato descriptors established jointly by the International Potato Center (CIP), Lima, Peru; The Asian Vegetable Research and Development Center (AVRDC), Taipei, Taiwan; and the International Board for Plant Genetics Resources (IBPGR), Rome, Italy (CIP, AVRDC, IBPGR. 1991. Descriptors for Sweet Potato. Huaman, Z., editor. International Board for Plant Genetic Resources, Rome, Italy, 134 pp.). Where dimensions, sizes, colors, and other characteristics are given, it is to be understood that such characteristics are approximations or averages set forth as accurately as practicable.

The descriptions reported herein are from a group of 58-day-old specimens grown individually in six-inch azalea pots. The plants were grown in Raleigh, NC, under commercial practice in a plastic-covered greenhouse, where, during the summer, day and night temperatures range between 30-40° C. and 22-26° C., respectively. After rooting, plants were treated with 200 ppm N 20-10-20 fertilizer weekly. Plant histories were taken in July 2023 in Raleigh, North Carolina. *Ipomoea batatas* 'NCORNSP-032SCRHI' has not been observed under all possible environmental conditions; therefore, the phenotype may vary under different environmental conditions such as season, temperature, light intensity, day length, cultural conditions, and the like, without however, any variance in the genotype.

Classification:

*Botanical name.*—*Ipomoea batatas* (L.) Lam.

*Common name.*—Ornamental Sweetpotato.

*Variety name.*—'NCORNSP-032SCRHI'.

Growth conditions: *Ipomoea batatas* 'NCORNSP-032SCRHI' has very good vigor and a moderate growth rate. In locations with mild winter conditions, *Ipomoea*

*batatas* 'NCORNSP-032SCRHI' will grow perennially; otherwise, it is an annual plant. Similar to other cultivated sweetpotatoes, wind or rain rarely cause much damage to 'NCORNSP-032SCRHI', but if damage does occur, the plant drops the damaged leaves and grows new shoots at nodes where the leaves were lost. Under low light levels in a greenhouse, 'NCORNSP-032SCRHI' can develop intumescence, which will remain on the affected foliage, but will be outgrown with new foliage.

Aboveground structure and coloration: FIGS. 1, 2, 3, 4, and 5 show the shape and coloration of a typical specimen of *Ipomoea batatas* 'NCORNSP-032SCRHI'. Color may vary somewhat due to temperature and nutrient stress. Overall, this cultivar is a moderately-compact, non-twining, semi-upright herbaceous plant that has an average height of about 19.9 cm and an average area spread of about 59.5 cm. The growth habit of this plant is to grow upright with shoots growing upward and outward.

Branches:

*Branching habit*.—Freely-branching with about 6-7 primary lateral branches coming off the stem. Dense foliage and no pinching is required to stimulate branching. Branch texture is slightly pubescent.

*Vegetative lateral branching*.—Length: about 21.2 cm. Diameter: about 0.5 cm. Internodes are short with an average length of about 1.3 cm.

*Secondary lateral shoots*.—No measurable secondary lateral shoots formed on the rated plants.

*Stem*.—Round and slightly pubescent with an upward, very strong, slightly flexible, non-brittle strength. Primary color: purple (RHS N77A).

*Adventitious roots*.—None.

Foliage: Leaves are alternate and tend to slightly spiral around the stem. They are simple and moderately lobed with five lobes. Leaf shape is somewhat variable as is size. (see FIG. 5).

*Quantity*.—Heavily foliated, with about 21.3 leaves per lateral branch.

*Mature leaf length*.—About 9.0 cm.

*Mature leaf width*.—About 12.0 cm.

*Leaf margin*.—Entire.

*Leaf apex*.—Apiculate.

*Leaf base*.—Cordate.

*Leaf texture*.—Glabrous texture and matte finish.

*Venation*.—Arcuate to cross-venulate.

*Color*.—Mature leaves are greyed-purple (RHS 187A) and typically range in color within the RHS 187A, 187B, 187C and 187D color codes. See also Table 1.

*Petiole*.—Petioles are held slightly upward and curve outward. Leaf petiole is smooth and glabrous. Length: about 10.7 cm. Diameter: about 0.2 cm. Primary color: greyed-purple (RHS 187A), secondary color: none.

TABLE 1

Leaf color of *Ipomoea batatas* 'NCORNSP-032SCRHI'.

| Leaf Structure | Upper Surface | Lower Surface |
|---|---|---|
| Mature Leaf | Greyed-Purple (RHS 187A) | Greyed-Purple (RHS N186C) |
| Young Leaf | Yellow-Green (RHS 152C-D) | Yellow-Green (RHS 146D) |

TABLE 1-continued

Leaf color of *Ipomoea batatas* 'NCORNSP-032SCRHI'.

| Leaf Structure | Upper Surface | Lower Surface |
|---|---|---|
| Vein - mature leaf | Greyed-Purple (RHS N186C) | Purple (RHS N79A) |
| Vein - young leaf | Yellow-Green (RHS 152C) | Yellow-Green (RHS 147D) |

Inflorescence: The production of flowers by 'NCORNSP-032SCRHI' is very sporadic and unobserved even under stressful conditions (e.g., drought, nutrient stress, cloudy weather). Shorter day lengths enhance flowering, but the precise photoperiod for flower induction is currently unknown.

Figure 6:
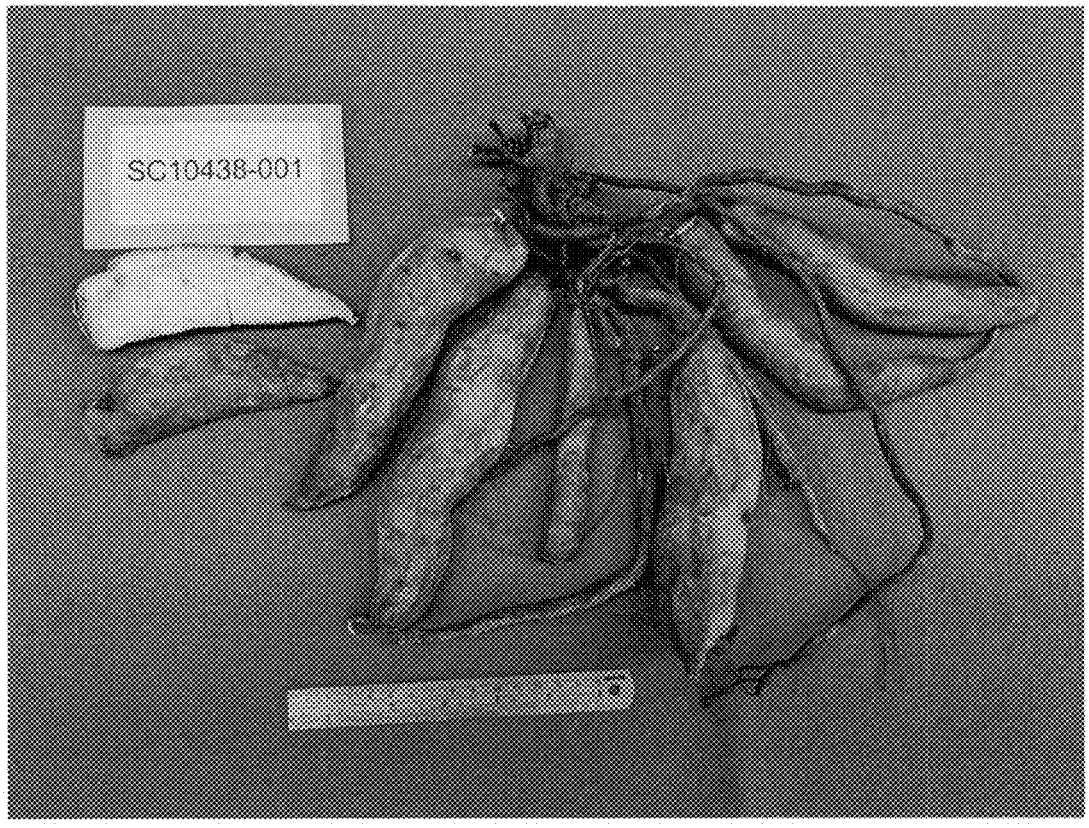
FIG. 6 is a color photograph showing the storage roots produced by *Ipomoea batatas* 'NCORNSP-032SCRHI' in the field, 130 days after planting.

Storage root coloration: *Ipomoea batatas* 'NCORNSP-032SCRHI' forms moderately sized underground storage roots that would typically fall below marketable significance based on the USDA Sweetpotato Storage Root Grade Standards (see FIG. 6). Fibrous roots are typically cream (RHS 155B). Storage roots that are formed possess a skin color of purple (RHS N77B). Storage roots have a yellow-white (RHS 158B) flesh color.

Disease or pest resistance. 'NCORNSP-032SCRHI' is susceptible to whiteflies and thrips in a greenhouse environment. 'NCORNSP-032SCRHI' is susceptible to damage by Japanese beetles under outdoor conditions. The susceptibility of 'NCORNSP-032SCRHI' to other known insects and pathogens of sweetpotato is unknown. Under low light conditions, slight edema may occur.

COMPARISON WITH OTHER *IPOMOEA BATATAS* CULTIVARS

'NCORNSP-032SCRHI' is distinct based on color uniformity, leaf shape, and plant habit. Of the common cultivars of ornamental sweetpotato, 'NCORNSP-032SCRHI' is best compared with the 'NCORNSP-026SCRH' (unpatented) and 'NCORNSP-030ILPL' (U.S. Plant Pat. No. 35,096) cultivars (Table 2). Like both 'NCORNSP-026SCRH' and 'NCORNSP-030ILPL', 'NCORNSP-032SCRHI' has leaves in the red-burgundy spectrum. However, 'NCORNSP-032SCRHI' is more consistently uniform in the red range throughout the season. Compared to 'NCORNSP-026SCRH', 'NCORNSP-032SCRHI' has slightly shorter leaves with slightly thinner, more forward pointed lobes. 'NCORNSP-032SCRHI' also has a more compact habit with less spread than 'NCORNSP-026SCRH'. Compared to 'NCORNSP-030ILPL', 'NCORNSP-032SCRHI' has significantly smaller leaves with fewer and thicker lobes.

'NCORNSP-032SCRHI' is distinct from its female parent, 'NC9729-169ORN', by its leaf shape, color uniformity and plant habit. 'NCORNSP-032SCRHI' is a lighter shade of red than 'NC9729-169ORN', and the color is more uniform throughout the season. 'NCORNSP-032SCRHI' also has fewer lobes that are thicker in width than 'NC9729-169ORN'. Lastly, 'NCORNSP-032SCRHI' has a less compact plant habit than 'NC9729-169ORN'.

TABLE 2

Comparison of 'NCORNSP-032SCRHI' with other *Ipomoea batatas* cultivars.

| Characteristic | 'NCORNSP-032SCRHI' | 'NCORNSP-026SCRH' | 'NCORNSP-030ILPL' |
|---|---|---|---|
| Plant Habit | Moderately compact, loosely upright habit | Moderately compact, semi-erect mounding habit | Moderately compact, loosely upright habit |
| Average Leaf Length and Width | Length: 9.0 cm Width: 12.0 cm | Length: 9.6 cm Width: 10.4 cm | Length: 12.8 cm Width: 15.1 cm |
| Foliage Color | Greyed-Purple (RHS 187A) | Greyed-Purple (RHS 187A) | Greyed-Purple (RHS 187A) |
| Leaf Shape | Moderately lobed, 5 lobes. | Moderately lobed, 3-5 lobes. | Very deeply lobed, 5-7 lobes. |

TABLE 2-continued

Comparison of 'NCORNSP-032SCRHI' with other *Ipomoea batatas* cultivars.

| Characteristic | 'NCORNSP-032SCRHI' | 'NCORNSP-026SCRH' | 'NCORNSP-030ILPL' |
|---|---|---|---|
| | Entire with an apiculate apex and a cordate base. | Entire with an apiculate apex and cordate base. | Entire with an apiculate apex and an auriculate base. |

We claim:

1. A new and distinct cultivar of *Ipomoea batatas* plant named 'NCORNSP-032SCRHI', substantially as illustrated and described herein.

* * * * *